US00PP27393P3

(12) United States Plant Patent
Chandra et al.

(10) Patent No.: US PP27,393 P3
(45) Date of Patent: Nov. 15, 2016

(54) ST. AUGUSTINEGRASS PLANT NAMED 'DALSA 0605'

(50) Latin Name: ***Stenotaphrum secundatum* (Walt.) Kuntze**
Varietal Denomination: DALSA 0605

(71) Applicant: The Texas A&M University System, College Station, TX (US)

(72) Inventors: Ambika Chandra, Dallas, TX (US); Anthony D. Genovesi, Dallas, TX (US); Milton C. Engelke, College Station, TX (US)

(73) Assignee: The Texas A&M University System, College Station, TX (US)

( * ) Notice: Subject to any disclaimer, the term of this patent is extended or adjusted under 35 U.S.C. 154(b) by 76 days.

(21) Appl. No.: 14/544,540

(22) Filed: Jan. 16, 2015

(65) Prior Publication Data

US 2016/0212912 P1 Jul. 21, 2016

(51) Int. Cl.
*A01H 5/12* (2006.01)

(52) U.S. Cl.
USPC ..... Plt./392

(58) Field of Classification Search
USPC ..... Plt./392
See application file for complete search history.

(56) References Cited

U.S. PATENT DOCUMENTS

PP9,395 P 12/1995 Kirkland et al.

OTHER PUBLICATIONS

Chandra et al. Registration of Dalsa0605 St Augustinegrass Journal of Plant Registrations 9(1):27-34,2014.*
Halloway K. New St Augustine hybrid promises better drought tolerance. The Dallas Morning New . Jun. 18, 2014.*
Bateman, "Notice to sod producers and growers relative to the naming and release of the new St. Augustine cultivar 'Raleigh'," N. C. Ag. Res. Serv., Raleigh, NC, 1980.
Busey, "Genetic diversity and vulnerability of St. Augustinegrass," *Crop Sci* 35:322-327, 1995.
Busey, "St. Augustinegrass, *Stenotaphrum secundatum* (Walt.) Kuntze," Ch. 20, p. 309-330. In Casler, M.D., and R.R. Duncan (eds.). Turfgrass Biology, Genetics, and Breeding, John Wiley & Sons., Inc., Hoboken, NJ, 2003.
Chandra et al. "Registration of 'DALSA 0605' St. Augustinegrass," *Journal of Plant Registrations* 9(1):27-34, 2014.
Genovesi et al., "Interploid St. Augustinegrass [*Stenotaphrum secundatum* (Walt.) Knutze] Hybrids Recovered by Embryo Rescue," *In Vitro Cell Dev Biol-Plant* 45(6):659-666, 2009.
Horn et al., "'Floratam' St. Augustinegrass: A fast growing new variety for ornamental turf resistant to St. Augustine decline and chinch bugs," *Florida Agric. Exp. Stn. Circ.* S-224, 1973.
Metz et al., "Comparison of screening methods to evaluate the response of St. Augustine grass to *Magnaporthe oryzae," Plant Path* 61(2):255-261, 2012.
Milla-Lewis et al., "Cytological and molecular characterization of genetic diversity in *Stenotaphrum," Crop Sci* 53(1):296-308, 2013.
Miller et al., "Turfgrass rooting characteristics of 'Palmetto', 'FX-10', and 'Floratam' St. Augustinegrasses and 'Pensacola' bahiagrass," In Box, J.J.E. (ed.). Root Demographics and Their Efficiencies in Sustainable Agriculture, 1998.
Holloway, "New St. Augustine hybrid promises better drought tolerance," *The Dallas Morning News,* available at <http://www.dallasnews.com/lifestyles/home-and-gardening/headlines/20140618-new-st.-augustine-hybrid-promises-better-drought-tolerance.ece>, published Jun. 18, 2014.
Schattenberg, "New St. Augustine grass hybrid uses less water, offers other advantages," available at <http://phys.org/news/2014-04-st-augustine-grass-hybrid-advantages.html>, Apr. 3, 2014.
Schattenberg, "AgriLife's Dallas center releases new water-efficient turfgrass," available at <http://soilcrop.tamu.edu/agrilifes-dallas-center-releases-new-water-efficient-turfgrass/>, posted Apr. 4, 2014.
Texas A&M Plant Breeding Bulletin, available at <http://soilcrop.tamu.edu/newsletters_bulletins/plant_breeding/OCTOBER%20Plant%20Breeding%20Bulletin%202014.pdf>, Oct. 2014.
Schattenberg, "AgriLife's Dallas center releases new water-efficient turfgrass," available at <http://today.agrilife.org/2014/04/02/dallas-center-turfgrass-release/>, Apr. 2, 2014.

* cited by examiner

*Primary Examiner* — Annette Para
(74) *Attorney, Agent, or Firm* — Dentons US LLP

(57) ABSTRACT

'DALSA 0605' is a new variety of St. Augustinegrass distinguished by having high tolerance to grey leaf spot disease, significantly reduced levels of fecundity and juvenile development of Southern chinch bugs, and superior drought resistance conferred through a combination of tolerance to drying soil, deep genetic rooting potential, and rapid recovery following drought, as disclosed herein.

6 Drawing Sheets

1

STATEMENT REGARDING FEDERALLY SPONSORED RESEARCH

This invention was made with government support under Grant No. 2010-51181-21064 awarded by the USDA-NIFA. The government has certain rights in the invention.

Latin name of the genus and species of the plant claimed: *Stenotaphrum secundatum* (Walt.) Kuntze.

Cultivar denomination: 'DALSA 0605'.

2

BACKGROUND OF THE INVENTION

The invention relates to a new and distinct cultivar of St. Augustinegrass named 'DALSA 0605'. 'DALSA 0605' is a first generation, embryo rescue-derived interploid hybrid resulting from a cross between TAES 5382 (African polyploidy) and 'Palmetto'. TAES 5382 is a germplasm introduction from Zimbabwe, Africa (PI 291594) obtained from Georgia. 'Palmetto' is a diploid variety disclosed under designation SS-100 (U.S. Plant Pat. No. 9,395).

'DALSA 0605' was a peduncle selection from Cleveland, Tex. in 2005 and was brought to Dallas, Tex. The variety was propagated in 2005/2006, and planted in a strip trial in 2006 in Dallas. 'DALSA 0605' was originally evaluated under the designation TAES 5471-18 and included in the 2011 Specialty Crops Research Initiative Shared Spaced Plant Nursery under the designation TXSA 19. 'DALSA 0605' is a vegetatively propagated, genetically stable, and uniform variety. 'DALSA 0605' is the first reported embryo rescue-derived interploid hybrid variety of St. Augustinegrass proposed for commercial release. 'Dalsa 0605' was first asexually propagated in a greenhouse in Dallas, Tex. in 2005-2006 using stolon nodes.

In comparison to its pollen donor, 'Palmetto', 'DALSA 0605' exhibits longer leaf blades and longer internodes. Internode and node diameter of 'DALSA 0605' is wider than 'Palmetto'. The leaf width of 'DALSA 0605' is similar to 'Palmetto'. 'DALSA 0605' is more tolerant to gray leaf spot disease as compared to 'Palmetto' and has sterile inflorescences unlike 'Palmetto', which is fertile.

Like its maternal parent, PI 291594, 'DALSA 0605' is highly tolerant to gray leaf spot disease and is sterile.

'DALSA 0605' has not been made publicly available more than one year prior to the filing date of this application.

SUMMARY OF THE INVENTION

The following are the most outstanding and distinguishing characteristics of 'DALSA 0605'. (1) 'DALSA 0605' is highly tolerant to the grey leaf spot disease caused by *Magnaporthe oryzae* Couch; (2) 'DALSA 0605' exhibits significantly reduced levels of fecundity and juvenile development of Southern chinch bugs (*Blissus insularis* Barber) as compared to 'Raleigh' and 'Texas Common'; (3) 'DALSA 0605' exhibits superior drought resistance conferred through a combination of tolerance to drying soil, deep genetic rooting potential compared to 'Floratam', rapid recovery following drought; (4) higher percent mortality of confined larvae of tropical sod webworm (*Herpetogramma phaeopteralis* Guenée) as compared to 'Raleigh'; and (5) adaptability to a wide-range of environmental conditions encountered across the Southern and Southeastern United States. Multi-location and multi-year field evaluation showed 'DALSA 0605' to exhibit percent establishment and turfgrass quality ratings comparable to commercial check varieties. 'DALSA 0605' is well suited for use in lawns, landscapes, and other recreational sites throughout the Southern and Southeastern United States. 'DALSA 0605' is a sterile interploid hybrid with no viable seed formation resulting in little chance of off-type contamination in the sod production fields.

BRIEF DESCRIPTION OF THE DRAWINGS

This new St. Augustinegrass variety is illustrated by the accompanying photographs. The colors shown are as true as can be reasonably obtained by conventional photographic procedures.

DETAILED BOTANICAL DESCRIPTION

The following detailed description sets forth the distinctive characteristics of St. Augustine variety 'DALSA 0605' as grown in Dallas, Tex.

Figure 1:
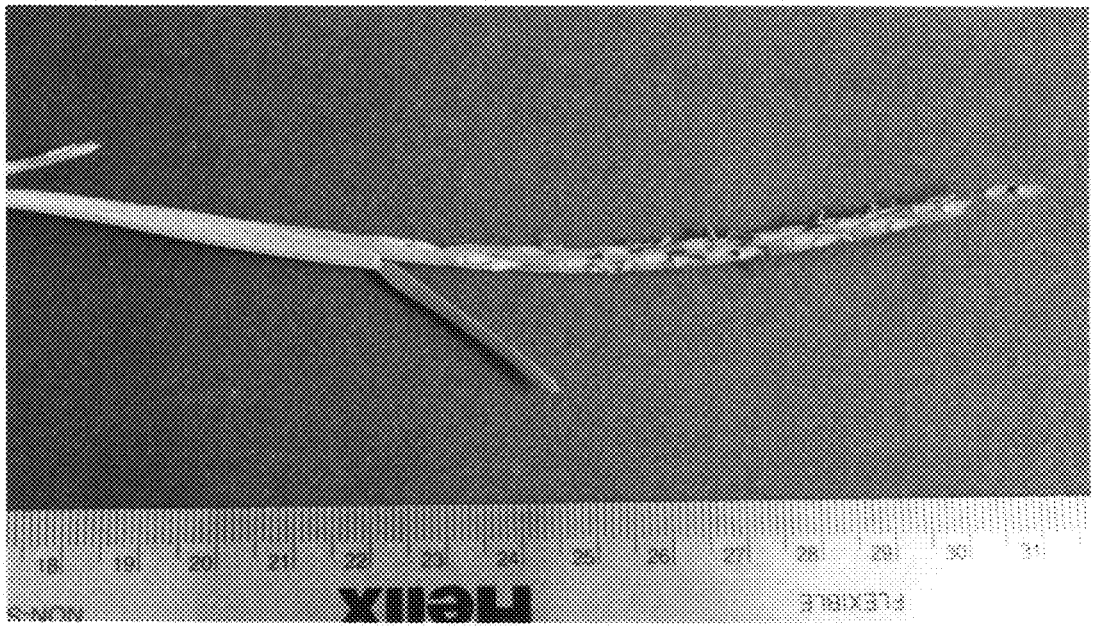
FIG. 1—Shows an inflorescence of 'DALSA 0605' depicting its anther and stigma color.
Figure 2:
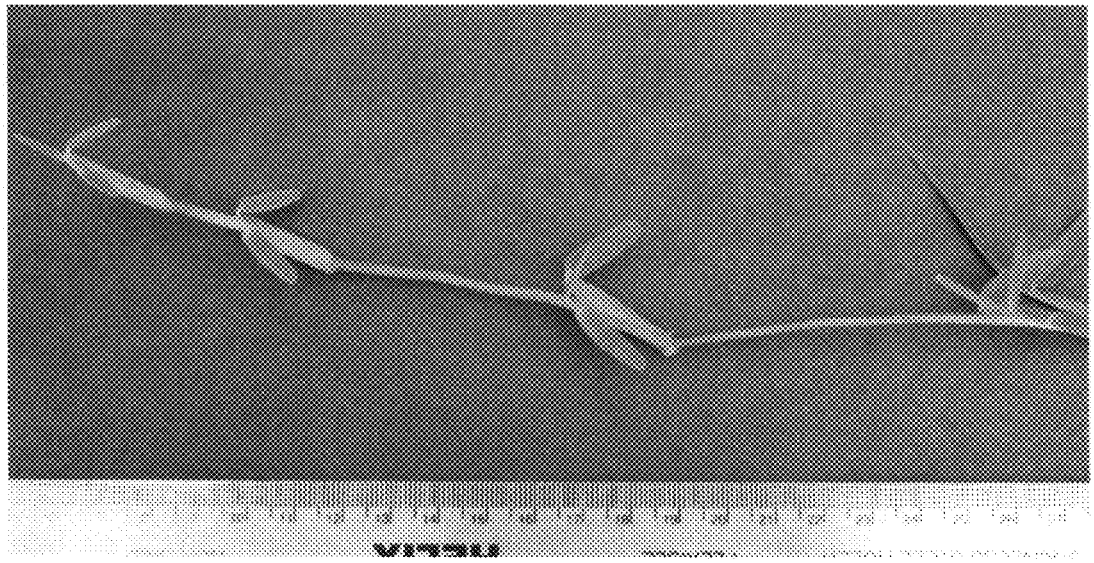
FIG. 2—Shows the purple coloration and internode length of a stolon of 'DALSA 0605'.

Morphology—Morphological data were obtained in June 2013 from three replicate 18.9-liter pots each of 'DALSA 0605', 'Floratam', 'Raleigh', and 'Palmetto' maintained under field conditions in Dallas, Tex. (Table 1). Leaf blade length was determined for the three tallest leaves in each of the three replicate pots for all four entries by measuring the distance between the base and the tip of the leaf. Leaf blade width was recorded for the same three tallest leaves at the widest point of the leaf blade. Internode length and diameter between the fifth and sixth nodes, and node diameter of the fourth node were measured for the three longest stolons in each pot. FIG. 1 shows an inflorescence of 'DALSA 0605' depicting its anther and stigma color, while FIG. 2 shows the purple coloration and internode length of a stolon of 'DALSA 0605'. Table 2 provides florescence length (cm) and the length of the flowering culm between 'DALSA'0605' and commercial check varieties.

TABLE 1

Morphological characteristics of 'DALSA 0605' and three commercial cultivars of St. Augustinegrass.

| Cultivar | Leaf blade length (mm) † | Leaf blade width (mm) ‡ | Internode length (mm) § | Internode diameter (mm) § | Node diameter (mm) § |
|---|---|---|---|---|---|
| 'DALSA 0605' | 321.3a | 7.5a | 65.3a | 2.8a | 4.2a |
| 'Floratam' | 225.7b | 8.2a | 53.0b | 2.7a | 4.8a |
| 'Palmetto' | 195.7bc | 6.7a | 46.7b | 2.0b | 2.8b |
| 'Raleigh' | 189.0c | 8.3a | 46.0b | 2.3ab | 3.2b |
| LSD¶ | 31.1 | 2.2 | 12.3 | 0.5 | 0.7 |

† Leaf blade length was determined by measuring the distance between the base and the tip of three tallest leaves in each of the three replicate pots. Mean of nine measurements.
‡ Leaf blade width was recorded at the widest point for three tallest leaves in each of the three replicate pots. Mean of nine measurements.
§ Internode length and diameter were measured between the $5^{th}$ and $6^{th}$ nodes for the three longest stolons in each of the three replicate pots. Node diameter was measured for the $4^{th}$ node. Mean of nine measurements.
¶Means in a column followed by the same letter(s) are not significantly different by Fisher's Protected Least Significant Difference (LSD) Test ($P \leq 0.05$).

TABLE 2

Comparison of inflorescence length (cm) and peduncle length between 'DALSA 0605' and commercial checks grown in five gal containers in Dallas, TX.

| Entry | Inflorescence length† | Flowering Culm length‡ |
|---|---|---|
| 'DALSA 0605' | 20.8a | 5.7a |
| 'Raleigh' | 18.7 | 6.3a |
| 'Floratam' | 20.3a | 4.6 |
| LSD¶$_{0.05*}$ | 1.7 | 1.2 |
| CV#, % | 3.7 | 9.4 |

* Significant at a probability level of 0.05.

†Inflorescence length measured in centimeters from the tip to the base on the inflorescence.

‡Flowering culm length measured in centimeters from the base of the inflorescence to the first node.

¶Means were separated using Fisher's LSD Test. (P > F = 0.05). Means with an 'a' rating were in the top statistical group.

#CV (Coefficient of Variation) indicates the percent variation of the mean in each column.

'DALSA 0605' has an upright, stoloniferous growth habit, i.e. the variety asexually reproduces through solons. 'DALSA 0605' has longer internode and leaf blade lengths as compared to all tested commercial checks. Similar to 'Floratam', 'DALSA 0605' may require more frequent mowing than cultivars with compact growth habits such as 'Raleigh' because of its faster leaf growth (elongation). The internode diameter of 'DALSA 0605' is in the same statistical group as 'Floratam' and 'Raleigh', and the node diameter is in the same statistical group as 'Floratam'. There were no significant differences in leaf blade width of 'DALSA 0605' in comparison to all tested commercial checks.

Field performance—'DALSA 0605' was evaluated in a strip trial from 2007 to 2010 in Dallas, Tex. Comparison data for 'DALSA 0605' and commercial check 'Raleigh' is presented in Table 3. Based on mean turfgrass quality, mean density, genetic color, fall color, and spring green-up, 'DALSA 0605' ranked number one in the trial with a total Turfgrass Performance Index (TPI; number of times the variety appeared in the top statistical group) of 16 as compared to Raleigh with a total TPI of 7.

Comparison data for 'DALSA 0605' and commercial checks 'Raleigh' and 'Captiva' from a replicated field trial from 2009 to 2011 in Dallas, Tex. are presented in Table 4. Data collected for mean turfgrass quality, spread, mean shoot density, genetic color, disease resistance (gray leaf spot), and leaf firing, showed that 'DALSA 0605' was ranked number one with a total TPI of 12 (Table 4) in comparison to 'Captiva' with a TPI of 6 and 'Raleigh' with a TPI of 5.

'DALSA 0605' (coded as TXSA 19) was evaluated in the Specialty Crops Research Initiative (SCRI) Shared Spaced Plant Nursery (SSPN), a multi-location progeny evaluation trial established in seven locations (Dallas and College Station, Tex.; Stillwater, Okla.; Raleigh, N.C.; Tifton and Griffin, Ga.; and Gainesville, Fla.) for a 2-year period, 2011 and 2012. Comparison data for 'DALSA 0605' and three commercial checks, 'Floratam', 'Raleigh', and 'Palmetto' are presented in Tables 5-7. Data demonstrating percent establishment in 2011 and 2012 showed 'DALSA 0605' and 'Palmetto' to be tied for the highest TPI of 12 (Table 5). For mean turfgrass quality ratings taken under an optimal irrigation regime across seven locations, 'DALSA 0605' performed similarly to 'Palmetto', 'Raleigh', and 'Floratam' with a total TPI of 7 (Table 6). When drought stress was imposed at five of seven locations in 2012, 'DALSA 0605' and 'Palmetto' exhibited a TPI of 5 followed by 'Raleigh' and 'Floratam', each with a TPI of 4 (Table 6). Overall, 'DALSA 0605' was tied with 'Palmetto' for a ranking of 1.5 based on percent establishment and turfgrass quality across seven locations during 2011 and 2012 (Table 7).

TABLE 3

Turfgrass performance characteristics recorded from 2007 to 2010 in a strip trial in Dallas, TX. Colors are in reference to the Munsell color chart for plant tissues.

| | Mean Turfgrass Quality† | | | | Mean Density‡ | | |
|---|---|---|---|---|---|---|---|
| Entry | 2007 | 2008 | 2009 | 2010 | 2008 | 2009 | 2010 |
| 'DALSA0605' | 6.5a* | 6.1a | 6.1a | 5.3a | 7.7a | 7.7a | 5.1a |
| 'Raleigh' | 6.4a | 5.2 | 4.8 | 4.5 | 6.4 | 5.1 | 5.2a |

| | Genetic Color§ | | | Fall Color¶ | | |
|---|---|---|---|---|---|---|
| Entry | 2008 | 2009 | 2010 | 2007 | 2008 | 2010 |
| 'DALSA0605' | 5.7a | 7.0a | 5.0a | 8.0a | 6.3a | 7.3a |
| 'Raleigh' | 5.3a | 6.3a | 4.7a | 4.3 | 4.7 | 7.3a |

| | Spring Green-up# | | | | |
|---|---|---|---|---|---|
| Entry | 2008 | 2009 | 2010 | TPI†† | Rank |
| 'DALSA0605' | 1.7a | 5.3a | 6.7a | 16 | 1 |
| 'Raleigh' | 1.3 | 3.0 | 6.0a | 7 | 2 |

†Turf quality rated on a scale of 1 to 9 where 1 = undesirable quality, 9 = ideal highest quality, and 5 = minimum acceptable quality.

‡Density rated on scale of 1 to 9 where 1 = bare ground and 9 = the highest number of plants per unit area.

§Genetic color rated on scale of 1 to 9 where 1 = being light green and 9 = dark green.

¶Fall color rated on a scale of 1 to 9 where 1 = being straw brown and 9 = dark green.

#Spring green-up rated on a scale of 1 to 9 where 1 = being straw brown and 9 = dark green.

††TPI is the Turf Performance Index, representing the number of times an entry appeared in the top statistical group, indicated by letter 'a'.

*Means were separated using Fisher's Least Significant Difference Test (P = 0.05).

TABLE 4

Turfgrass performance characteristics recorded from 2009 to 2011 in a replicated field trial in Dallas, TX. Colors are in reference to the Munsell color chart for plant tissues.

| | Mean Turfgrass Quality† | | | Mean Density‡ | | |
|---|---|---|---|---|---|---|
| Entry | 2009 | 2010 | 2011 | 2009 | 2010 | 2011 |
| 'DALSA0605' | 5.2a§§ | 5.7a | 5.6a | 6.1a | 6.1a | 7.3a |
| 'Captiva' | 4.2 | 4.5 | 3.8 | 5.4a | 5.9a | 4.6 |
| 'Raleigh' | 4.1 | 4.5 | 3.2 | 4.9a | 5.4a | 4.4 |

| | Genetic Color§ | | | Disease | |
|---|---|---|---|---|---|
| Entry | 2009 | 2010 | 2011 | Resistance¶ | Spread# |
| 'DALSA0605' | 8.0a | 6.0a | 7.0a | 8.0a | 8.0a |
| 'Captiva' | 8.0a | 5.7a | 6.7a | 7.0a | 5.0 |
| 'Raleigh' | 7.0a | 5.0a | 5.7 | 6.3 | 6.3 |

| Entry | Leaf Firing†† | TPI‡‡ | Rank |
|---|---|---|---|
| 'DALSA0605' | 8.3a | 12 | 1 |
| 'Captiva' | 5.2 | 6 | 2 |
| 'Raleigh' | 6.0a | 5 | 3 |

†Turf quality rated on a scale of 1 to 9 where 1 = undesirable quality, 9 = ideal highest quality, and 5 = minimum acceptable quality.

‡Density rated on scale of 1 to 9 where 1 = bare ground and 9 = the highest number of plants per unit area.

§Genetic color rated on scale of 1 to 9 where 1 = being light green and 9 = dark green.

¶Disease resistance (Gray leaf spot) was rated on a scale of 1 to 9 where 1 = susceptible and 9 = no damage.

#Spread was rated on a scale of 1 to 9 where 1 = original plug size and 9 = Full plot coverage.

††Drought tolerance assessed as leaf firing on a 1 to 9 visual rating scale with 1 = 100% leaf firing and 9 = no leaf firing.

‡‡TPI is the Turf Performance Index, representing the number of times an entry appeared in the top statistical group, indicated by 'a'.

§§Means were separated using Fisher's Least Significance Difference Test (P = 0.05).

TABLE 5

Mean percent coverage of 'DALSA 0605' in comparison to commercial checks from seven locations during 2011 and 2012.

| | Mean Percent Coverage† | | | | | |
|---|---|---|---|---|---|---|
| | College Station TX | | Dallas TX | | Gainesville FL | |
| Entry | 2011 | 2012 | 2011 | 2012 | 2011 | 2012 |
| 'DALSA0605' | 52.5a¶ | 97.5a | 9.3a | 75.0a | 24.2 | 67.5a |
| 'Palmetto' | 45.8a | 100.0a | 13.2a | 93.8a | 43.0a | 77.5a |
| 'Floratam' | 75.8a | 100.0a | 17.4a | 96.3a | 24.3 | 67.5a |
| 'Raleigh' | 70.8a | 100.0a | 1.4 | 43.8 | 35.8a | 72.5a |

| | Mean Percent Coverage† | | | | |
|---|---|---|---|---|---|
| | Griffin GA | | Tifton GA | | Jackson Spring NC |
| Entry | 2011 | 2012 | 2011 | 2012 | 2011 |
| 'DALSA0605' | 55.6a | 72.5a | 62.3a | 73.3a | 55.0a |
| 'Palmetto' | 61.3a | 58.8a | 52.7a | 57.5 | 46.7a |
| 'Floratam' | 55.0a | 75.0a | 58.5a | 59.5 | 83.3a |
| 'Raleigh' | 45.0a | 56.3a | 35.5 | 57.1 | 48.3a |

| | Mean Percent Coverage† | | | |
|---|---|---|---|---|
| | Stillwater OK | | Grand | |
| Entry | 2011 | 2012 | Mean | TPI†† |
| 'DALSA0605' | 56.7a | 94.1a | 61.2 | 12 |
| 'Palmetto' | 43.8a | 81.7a | 59.7 | 12 |
| 'Floratam' | 47.9a | 81.7a | 64.8 | 11 |
| 'Raleigh' | 32.1 | 74.5 | 51.8 | 7 |

†Percent Coverage was estimated on a percent basis from 1 = Original plug size to 100 percent = full plot coverage.
‡Turf quality rated on a scale of 1 to 9 where 1 = undesirable quality, 9 = the ideal highest quality of turf and 5 = the minimum acceptable turf quality.
††TPI is the Turf Performance Index representing the number of times an entry appeared in the top statistical group, indicated by 'a'.
‡Means were separated using Fisher's LSD Test (P = 0.05).

TABLE 6

Mean turfgrass quality of DALSA0605 in comparison to commercial checks during normal (2011 and 2012) and dry down conditions (2012) across the Southern and Southeastern U.S.

| | Mean Turfgrass Quality‡ | | | |
|---|---|---|---|---|
| Entry | College Station TX | Dallas TX | Gainesville FL | Griffin GA |
| 'DALSA0605' | 5.4a | 4.7a | 5.6a | 7.0a |
| 'Palmetto' | 5.2a | 4.4a | 4.3a | 6.0a |
| 'Raleigh' | 5.4a | 2.8a | 3.9a | 5.7a |
| 'Floratam' | 5.5a | 4.5a | 4.6a | 6.8a |

| | Mean Turfgrass Quality‡ | | | | |
|---|---|---|---|---|---|
| Entry | Tifton GA | Jackson Spring NC | Stillwater OK | Grand Mean | TPI†† |
| 'DALSA0605' | 6.1a | 5.6a | 5.8a | 5.8 | 7 |
| 'Palmetto' | 6.0a | 5.9a | 5.1a | 5.3 | 7 |
| 'Raleigh' | 4.8a | 5.7a | 5.2a | 4.8 | 7 |
| 'Floratam' | 6.3a | 4.7a | 6.3a | 5.6 | 7 |

TABLE 6-continued

Mean turfgrass quality of DALSA0605 in comparison to commercial checks during normal (2011 and 2012) and dry down conditions (2012) across the Southern and Southeastern U.S.

| | Dry Down Mean Turfgrass Quality‡ in 2012 | | | | |
|---|---|---|---|---|---|
| Entry | College Station TX | Dallas TX | Gainesville FL | Jackson Spring NC | Stillwater OK |
| 'DALSA0605' | 5.0a | 6.5a | 3.6a | 5.0a | 4.8a |
| 'Palmetto' | 4.3a | 5.3a | 2.9a | 6.8a | 5.0a |
| 'Raleigh' | 5.0a | 4.0 | 3.9a | 6.8a | 5.0a |
| 'Floratam' | 5.8a | 5.3a | 3.9a | 4.0 | 4.5a |

| Entry | Grand Mean | TPI†† |
|---|---|---|
| 'DALSA0605' | 5.0 | 5 |
| 'Palmetto' | 4.9 | 5 |
| 'Raleigh' | 4.9 | 4 |
| 'Floratam' | 4.7 | 4 |

†Percent Coverage was estimated on a percent basis from I = Original plug size to 100 percent = full plot coverage.
‡Turf quality rated on a scale of 1 to 9 where 1 = undesirable quality, 9 = the ideal highest quality of turf and 5 = the minimum acceptable turf quality.
††TPI is the Turf Performance Index representing the number of times an entry appeared in the top statistical group, indicated by 'a'.
¶Means were separated using Fisher's LSD Test (P = 0.05).

TABLE 7

Cumulative turfgrass performance indices of DALSA 0605 in comparison to the commercial checks.

| Entry | Mean Turf Quality | Mean TQ Dry Down | Mean Percent Cover | Total TPI†† | Rank |
|---|---|---|---|---|---|
| 'DALSA0605' | 7 | 5 | 12 | 24 | 1.5 |
| 'Palmetto' | 7 | 5 | 12 | 24 | 1.5 |
| 'Floratam' | 7 | 4 | 11 | 22 | 3 |
| 'Raleigh' | 7 | 4 | 7 | 18 | 4 |

† Percent Coverage was estimated on a percent basis from 1 = Original plug size to 100 percent = full plot coverage.
‡Turf quality rated on a scale of 1 to 9 where 1 = undesirable quality, 9 = the ideal highest quality of turf and 5 = the minimum acceptable turf quality.
††TPI is the Turf Performance Index representing the number of times an entry appeared in the top statistical group, indicated by 'a'.
¶Means were separated using Fisher's LSD Test (P = 0.05).

Figure 3:
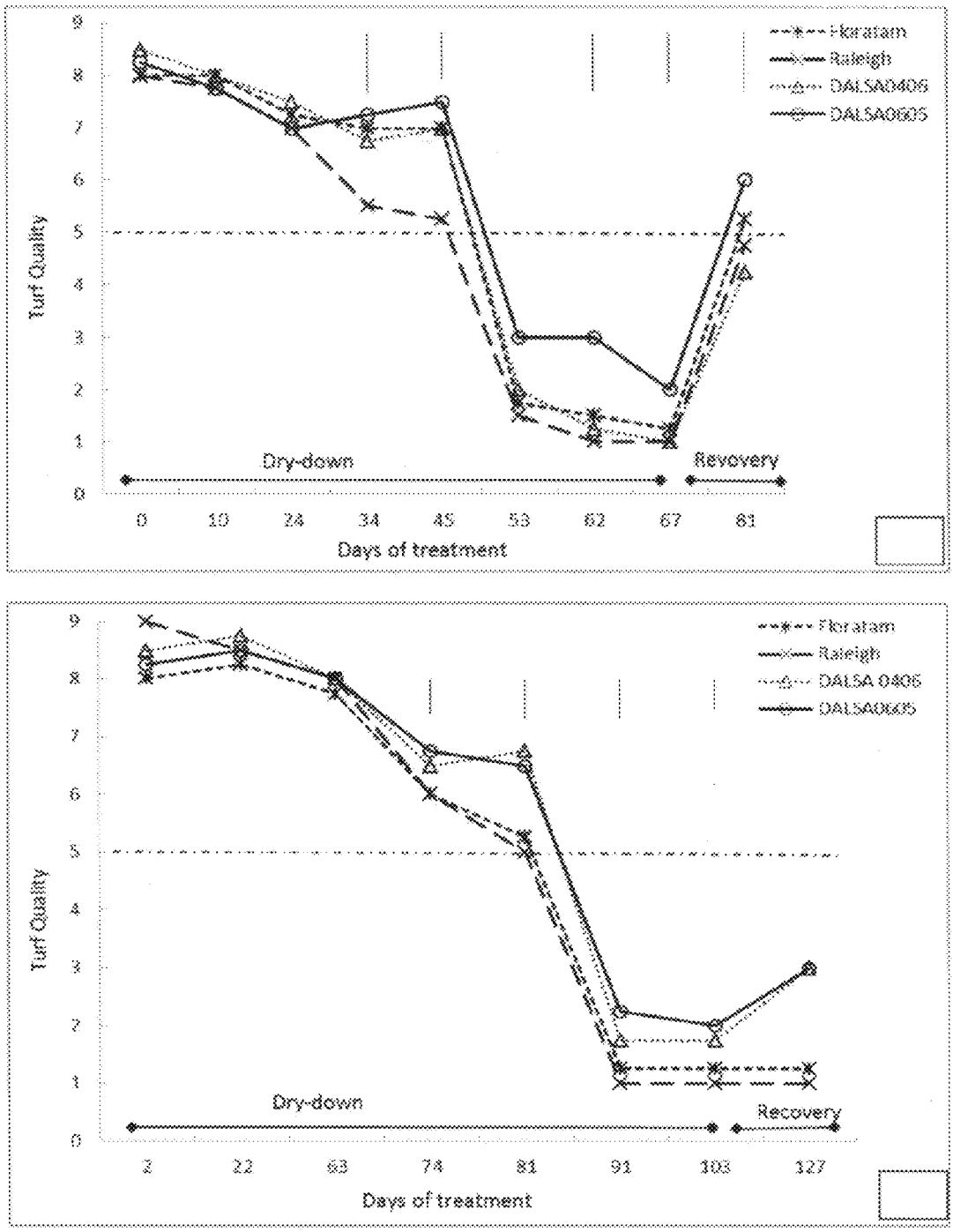
FIGS. 3*a* and 3*b*—Shows response and recovery of 'DALSA 0605' following prolonged drought stress in two separate greenhouse experiments. (3*a*, experiment 1; 3*b*, experiment 2) conducted in Dallas, Tex. Vertical bars indicate least significant difference (LSD) values where significant differences were detected (P=0.05) for comparison between genotypes at a given day of treatment. The horizontal dotted line indicates the minimum acceptable turf quality.

Drought stress response—'DALSA 0605' was evaluated through competitive dry-down studies conducted in Dallas, Tex. to screen for tolerance to drying soil and recovery following drought. In experiment 1, during the dry-down period, the turfgrass quality of all entries declined during the course of the dry-down period (no watering) in both experiments (FIGS. 3*a* and 3*b*), primarily due to leaf tissue firing. In experiment 1, the higher turfgrass quality ratings of 'DALSA 0605' were obtained when compared to 'Floratam', 'Raleigh', and 'DALSA 0406' during dry-down period (FIG. 3*a*). At 34 and 45 days of no watering, turfgrass quality of 'DALSA0605', 'DALSA0406', and 'Floratam' was significantly higher than 'Raleigh'. At 62 and 67 days of no watering, 'DALSA 0605' and 'Floratam' exhibited significantly higher turfgrass quality than 'DALSA 0406' and 'Raleigh'. Within 13 days of re-watering, 'DALSA 0605' and 'Floratam' were the only entries to recover to an acceptable turfgrass quality (≥5).

In experiment 2, a longer dry-down was provided. Throughout much of the dry-down, the turfgrass quality of 'DALSA 0605' and 'DALSA 0406' was significantly better than 'Raleigh' and 'Floratam'. After 91 days of dry-down, turfgrass quality for 'DALSA 0605' was significantly higher than that for 'DALSA 0406', 'Raleigh', and 'Floratam'.

After 103 days, 'Raleigh' and 'Floratam' were completely dead and did not recover following re-watering in contrast to 'DALSA 0605' and 'DALSA 0406' (FIG. 3*b*). By maintaining superior quality under increasing drought stress, 'DALSA 0605' demonstrates superior drought tolerance relative to other commercial St. Augustinegrass cultivars. This combined with an ability to rapidly recover from drought once irrigation is resumed suggests it would be well adapted for use in landscapes where irrigation frequency or amount is restricted during water conservation periods.

General observational data from multiple locations and years have indicated that 'DALSA 0605' possesses excellent drought quality, maintaining excellent color and delayed leaf wilt/firing during periods of limited water availability as compared to other St. Augustinegrass germplasm.

Figure 4:
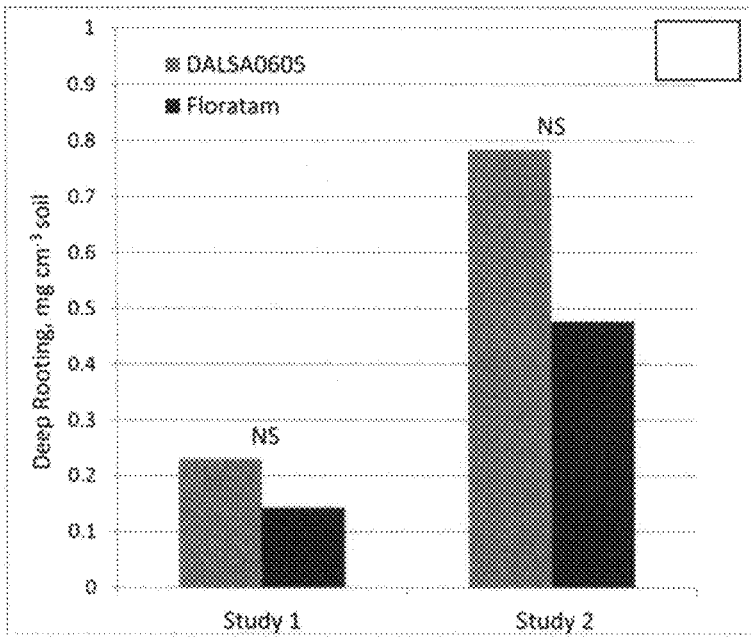
FIGS. 4*a* and 4*b*—Shows the deep rooting potential of 'DALSA 0605' compared to 'Floratam' St. Augustinegrass from greenhouse rooting column studies in College Station, Tex. 4*a* shows the total deep (46-92 cm depth) root length density for spring (study 1) and summer (study 2) studies. 4*b* shows the total root length density of deep roots as determined through root scanning. Evaluations were made 35 days following sod establishment. Means were not significantly (NS) different based on Fishers LSD ($\alpha$=0.05).
Figure 4:
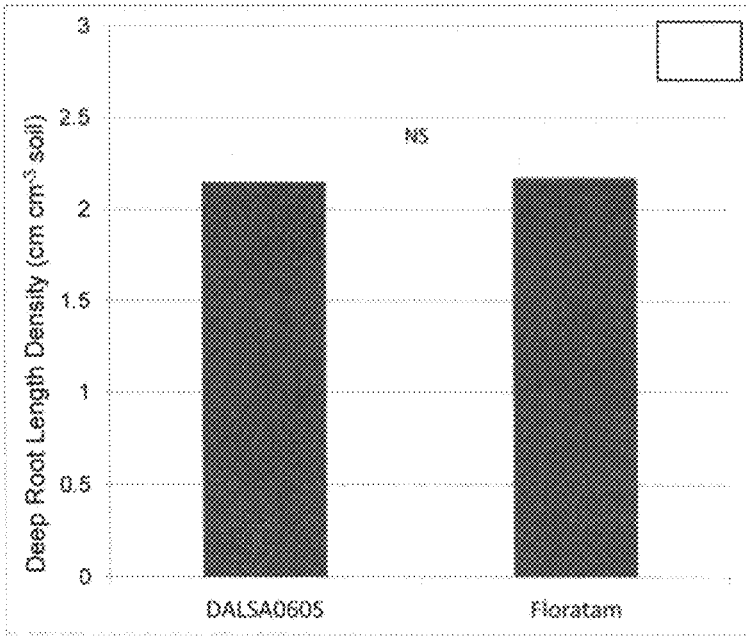

To examine the drought avoidance aspects of 'DALSA 0605' in more detail, rooting evaluations were conducted in College Station, Tex. during 2013 (FIG. 4). A trend toward greater deep (46-92 cm depth) root development in 'DALSA 0605' relative to 'Floratam' was observed in both experiments (FIG. 4*a*), but differences were not significant in either study. When pooled across studies, 'DALSA 0605' exhibited greater deep rooting development compared to 'Floratam', however differences were not significant. Total root length (cm of roots within the 46-92 cm depth of soil volume was also nearly identical between 'DALSA 0605' and 'Floratam' (FIG. 4*b*). Deep rooting has been considered a primary aspect of drought avoidance in turfgrasses. These rooting data emphasize that 'DALSA 0605' possesses comparable deep rooting potential to 'Floratam', which is currently the industry standard for drought avoidance.

Figure 5:
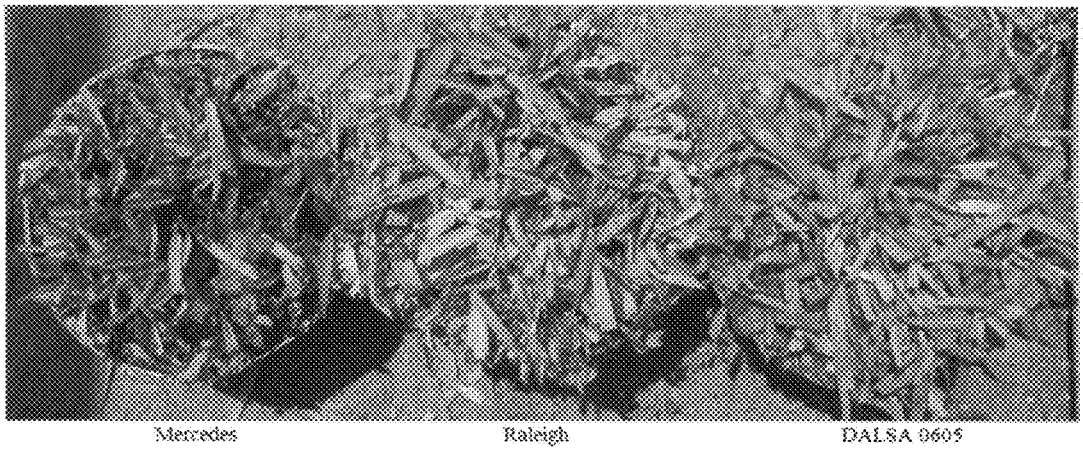
FIG. 5—Shows 'DALSA 0605' expressing high levels of tolerance to the gray leaf spot disease as compared to 'Mercedes' and 'Raleigh' in a study conducted in 2009 in Dallas, Tex. under field conditions.
Figure 6:
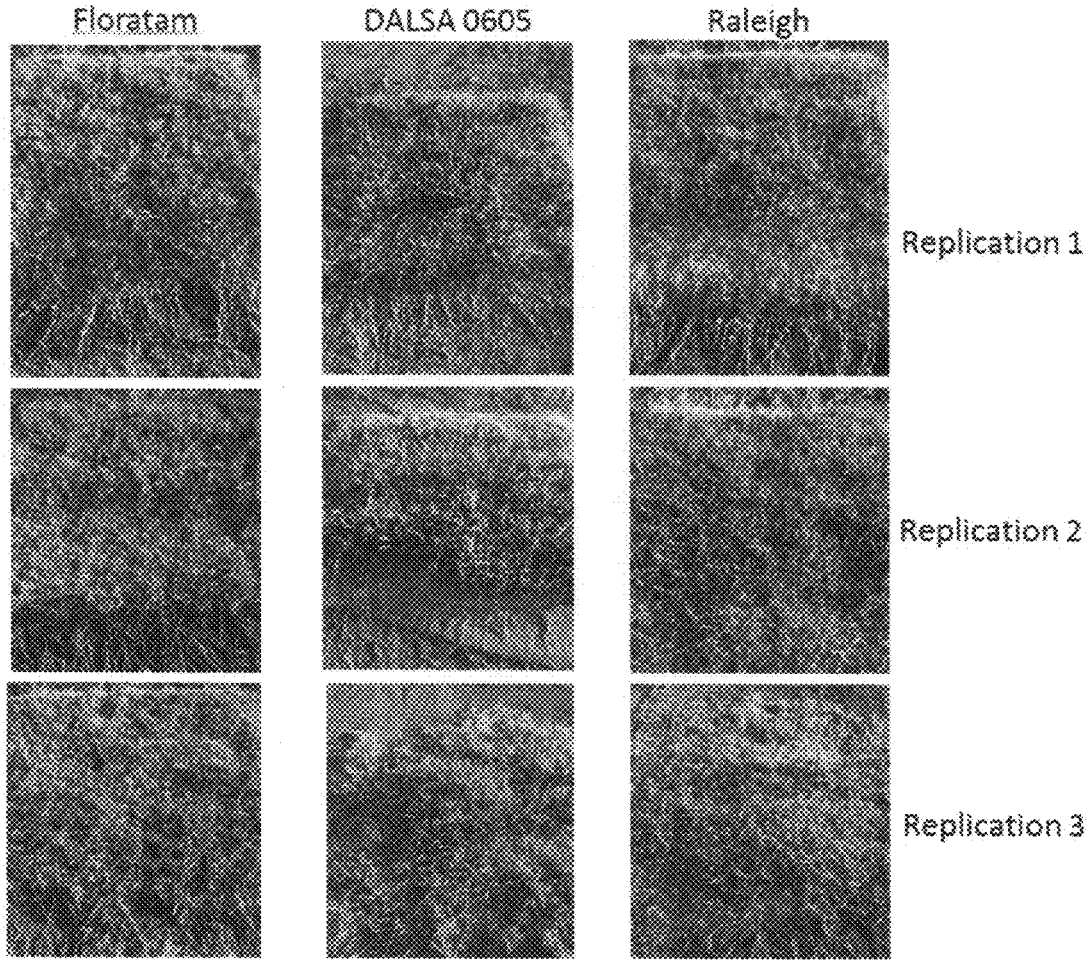
FIG. 6—Shows 2013-2014 winter survival of 'DALSA 0605' in comparison to 'Floratam' and 'Raleigh'. Pictures taken on May 1, 2014 in Dallas, Tex.

Disease and insect pest tolerance—In order to evaluate the disease resistance/susceptibility of 'DALSA 0605' to the gray leaf spot fungal disease, whole plant, detached stolon, and detached leaf assays of 8 commercial and 9 advanced breeding lines of St. Augustinegrass, including 'DALSA 0605', were conducted under growth chamber conditions and whole plant screening under field conditions. FIG. 5 shows the high levels of tolerance to the gray leaf spot disease for 'DALSA 0605' as compared to 'Mercedes' and 'Raleigh' in a study conducted in 2009 in Dallas, Tex. under field conditions. Based on lesion size and severity ratings, Metz et al. (*Plant Pathology* 61(2):255-261, 2012) showed that TAES 5382 (polyploidy maternal parent) and 'DALSA 0605' were consistently classified as highly resistant or resistant using the rank-sum method analysis. 'Palmetto' (diploid pollen parent) was classified as susceptible.

Susceptibility to the Southern chinch bug was also evaluated by allowing a population of chinch bugs to reproduce and develop as a population through one generation. At the end of the experiment all nymphs and adults were collected from the cages to determine susceptibility for each genotype. 'DALSA 0605', 8 other advanced breeding lines, and 'Floratam', 'Raleigh', and 'Texas Common' were compared for their acceptability as hosts. Comparison data for 'DALSA 0605' and commercial checks, 'Floratam', 'Captiva', 'Texas Common', and 'Raleigh' are presented in Table 8. No nymphs and less than 10 adults were recovered from 'DALSA 0605'. Population development on 'DALSA 0605' was significantly lower for 'Raleigh' and 'Texas Common' but not significantly different from 'Floratam', which had originally been identified as Southern chinch bug resistant.

TABLE 8

Development of Southern chinch bugs through one generation on St. Augustinegrass in a no-choice cage greenhouse test in Dallas, TX.

| | Mean Population per Cage | | |
|---|---|---|---|
| Genotype | Total Nymphs | Total Adults | Total Bugs |
| 'DALSA 0605' | 0.0d | 9.8b | 9.8e |
| 'Floratam' | 0.8d | 9.5b | 10.3e |
| 'Captiva' | 20.3bcd | 9.0b | 29.3cde |
| 'Texas Common' | 54.0ab | 9.8b | 63.8bc |
| 'Raleigh' | 103.0a | 15.5ab | 118.5a |

*Means in a column followed by the same letter are not significantly different by Fisher's Protected LSD Test (P = 0.05).

'DALSA 0605' along with 9 other advanced breeding lines and 'Raleigh' were evaluated for resistance to the tropical sod webworm. Comparison data for 'DALSA 0605' and the commercial check 'Raleigh' are provided in Table 9. 'DALSA 0605' did not cause significant mortality or reduced larval weight of tropical sod webworm after 15 days in a no-choice feeding study, but rather provided a significant 20% mortality at pupation and a significant 36% mortality at adult emergence (Table 9). Table 10 provides additional morphological characteristics for 'DALSA 0605'.

TABLE 9

Resistance to tropical sod webworm among cultivars of St. Augustinegrass in laboratory no-choice tests in Dallas, TX.

| | 15-day-old larvae | | Pupa | | |
|---|---|---|---|---|---|
| Genotype | % mort[†,#] | wt (mg)[‡] | % mort[†,#] | wt (mg)[§] | d to pupa[¶] |
| 'Raleigh' | 0.0b | 34.7b | 8.0ab | 40.3cd | 22.7ab |
| 'DALSA 0605' | 4.0ab | 44.5cd | 20.0a | 41.8bcd | 20.8e |

| | Adult | |
|---|---|---|
| Genotype | % mort[†,#] | d to adult[¶] |
| 'Raleigh' | 12.0bcd | 31.8ab |
| 'DALSA 0605' | 36.0a | 30.2cde |

[†]Mean % of larvae mortality (mort) at 15 days after egg hatch, % mortality at pupation and % mortality at adult emergence.
[‡]Mean weight (wt) of surviving larvae after feeding on each genotype for 15 d.
[§]Mean weight for only those individuals that pupated (weight taken within 1 d of pupation).
[¶]Mean number of days from egg hatch to pupation and adult emergence for larvae fed on each genotype.
[#]Data were transformed to arcsine for analysis; untransformed means presented here.
*Means in a column followed by the same letter are not significantly different by Fisher's Protected LSD Test (P = 0.05)

TABLE 10

Additional morphological characteristics of 'DALSA 0605'

| CHARACTERISTIC | 'DALSA 0605' | 'Delmar' |
|---|---|---|
| Growth Habit | Upright | |
| Leaf Blade | | |
| Barbs | Present | |
| Hairiness | Glabrous | |
| Leaf Sheath (adaxial margin) | Long hairs present | |
| Leaf Collar (adaxial margin) | Hairy | |
| Flowering Shoot (at anthesis) | | |
| Height from soil level to top of terminal raceme (cm) | 29 | 26.3 |
| Raceme length, lowest spikelet to tip of raceme (cm) | 9 | 6.2 |
| Number of spikelets/raceme | 32 | |

TABLE 10-continued

| Additional morphological characteristics of 'DALSA 0605' | | |
|---|---|---|
| CHARACTERISTIC | 'DALSA 0605' | 'Delmar' |
| Spikelet | | |
| Length (mm) | 4.3 | 4 |
| First glume length (mm) | 0.8 | 1.2 |
| Second glume length (mm) | 0.8 | 1.2 |
| Palea length (mm) | 4 | 4.1 |
| Lemma length (mm) | 3.8 | 4 |

TABLE 10-continued

| Additional morphological characteristics of 'DALSA 0605' | | |
|---|---|---|
| CHARACTERISTIC | 'DALSA 0605' | 'Delmar' |
| Insects/Diseases | | |
| St. Augustine decline virus | Susceptible | |
| Seeds | No seeds/sterile | |

What is claimed is:

1. A new and distinct variety of St. Augustinegrass called 'DALSA 0605' as shown and described herein.

* * * * *

Mercedes Raleigh DALSA 0605